United States Patent [19]

Hamada et al.

[11] Patent Number: 4,776,023

[45] Date of Patent: Oct. 4, 1988

[54] PATTERN INSPECTION METHOD

[75] Inventors: Toshimitsu Hamada; Mineo Nomoto, both of Yokohama; Kozo Nakahata, Chigasaki, all of Japan

[73] Assignee: Hitachi, Ltd., Tokyo, Japan

[21] Appl. No.: 850,681

[22] Filed: Apr. 11, 1986

[30] Foreign Application Priority Data

Apr. 12, 1985 [JP] Japan ................................. 60-76389

[51] Int. Cl.$^4$ ............................................. G06K 9/64
[52] U.S. Cl. ........................................... 382/8; 382/34
[58] Field of Search .................... 382/8, 27, 34, 54, 55

[56] References Cited

U.S. PATENT DOCUMENTS

| | | | |
|---|---|---|---|
| 4,010,446 | 3/1977 | Kawa | 382/55 |
| 4,578,765 | 3/1986 | Barker | 382/54 |
| 4,614,430 | 9/1986 | Hara et al. | 382/8 |
| 4,623,256 | 11/1986 | Ikenaga et al. | 382/8 |
| 4,628,531 | 12/1986 | Okamoto et al. | 382/8 |
| 4,648,053 | 3/1987 | Fridge | 382/8 |
| 4,651,341 | 3/1987 | Nakashima et al. | 382/8 |
| 4,668,982 | 5/1987 | Tinnerino | 382/8 |

FOREIGN PATENT DOCUMENTS

| | | |
|---|---|---|
| 2830846 | 1/1979 | Fed. Rep. of Germany. |
| 2912894 | 4/1980 | Fed. Rep. of Germany. |
| 59-24361 | 8/1984 | Japan. |

OTHER PUBLICATIONS

Hara et al, "Automatic Visual Inspection of LSI Photomasks", 5th *Int. Conf. on Pattern Recognition*, Dec. 1980, pp. 273–279.

Okamoto et al, "An Automatic Visual Inspection System for LSI Photomasks", 7th *Int. Conf. on Pattern Recognition*, Jul.–Aug. 1984, pp. 1361–1364.

*Primary Examiner*—Leo H. Boudreau
*Attorney, Agent, or Firm*—Antonelli, Terry & Wands

[57] ABSTRACT

Two kinds of image corresponding to a reference pattern and a pattern to be inspected are converted into binary images and local images cut out from the binary images are compared with each other to detect differences between the cut out images and recognize these differences as a defect. One of the main subjects of the inspecting method is to moderate excess sensitivity to the different portions to the extent of allowing non-serious actual defects. By setting don't care areas each of which consists of one pixel row neighboring on a binary boundary line in the image, and comparing the remaining portions of the images other than the don't care areas by logical processing it is possible to detect various defects without regarding the quantization error as a defect.

3 Claims, 7 Drawing Sheets $i, j = 1 \sim 5$ $\ell, k = 0 \sim 2$

▨ : DON'T CARE AREA

| | DEFECT APPEARANCES | EXTRACTION OPERATOR |
|---|---|---|
| (a) |  | $a_1$ $a_2$    $b_1$ $b_2$ |
| (b) |  | $a_1$   $b_1$ <br> $a_2$ $c_1$ $c_2$ $c_3$ $b_2$ <br> $a_3$   $b_3$ |
| (c) |  | $a_1$ $a_2$ $a_3$ <br> $c_1$ <br> $c_2$ <br> $c_3$ <br> $b_1$ $b_2$ $b_3$ |
| (d) |  | $a_4$ $a_3$ $a_2$ $a_1$ <br> $a_5$ <br> $a_6$   $b_1$ $b_2$ <br> $a_7$   $b_3$ $b_4$ |

PATTERN INSPECTION METHOD

BACKGROUND OF THE INVENTION

1. Field of the Invention

The present invention relates to pattern recognition technology for inspecting a wiring pattern on a printed wiring board, integrated circuit, or the like, and more particularly to a comparison inspection method in which two patterns having the same shape are compared with each other to detect that portion of one pattern which has a state different from the state of a corresponding portion of the other pattern, to recognize that portion as a defect.

2. Description of the Prior Art

In general, when the image of an integrated circuit pattern formed on a photo-mask or other patterns is inspected, it is necessary to prepare a reference image and an image to be inspected. These images are optically superimposed and then compared visually, to find a position where the images are different from each other, thereby detecting the presence of a defect. Accordingly, there arises a problem that, when an operator gets tired, the probability of missing the defect is increased.

In view of the above, a feature comparing method has been developed in which each of the reference image and the to-be-inspected image is delivered from an imaging device in the form of an image signal, and two image signals thus obtained are compared with each other to automatically detect a defect. In this method, however, owing to the possibility of a drawing error in forming a circuit pattern from a designed pattern (namely, reference pattern) and a positioning error of each image, an alignment error of two images is unavoidable. A comparison an inspection apparatus for a two-dimensional image is disclosed in Japanese Patent Application Unexamined Publication No. 59-24361. This apparatus can detect both a defect as large as a circuit pattern and a very small defect, without regarding a complicated, fine, normal circuit pattern itself as a defect when the normal circuit pattern deviates from a reference pattern within an allowable range of alignment error.

In this apparatus, two image signals delivered from a pair of imaging devices are converted into binary signals, and a predetermined memory element connected to inputs of a logical network is used for each of the binary signals so as to detect boundary lines parallel to the coordinate axes of a rectangular coordinate system. In order to detect the boundary lines accurately, it is necessary to use various kinds of memory elements, that is, it is necessary to prepare a memory element for detecting a boundary line which makes an angle of 45° with the coordinate axis and another memory element for detecting a corner portion of a pattern. As a result, there arises a problem that a logical network receiving the contents of each memory element becomes large in scale, that is, the apparatus is required to have large-scale hardware. While, if a complicated pattern is inspected by using only a few kinds of memory elements, some defects will be overlooked, and false information will be provided.

Next, the drawbacks of the prior art will be explained in detail. Let us consider a case where a pattern having only boundary lines parallel to X- and Y-directions (which make right angles with each other) is inspected, for the sake of simplicity. FIG. 8 shows extraction operators necessary for inspecting a pattern by the feature comparing method. Each of the extraction operators shown in FIG. 8 is a kind of memory element. In this case, that irregularity of a two-dimensional pattern which corresponds to two or more pixels, cannot be regarded as a quantization error, but is judged to be a defect. Now, an extraction operator (hereinafter referred to as an "operator") shown in part (a) of FIG. 8 for extracting a boundary line will be explained below, by way of example. The operator is moved on both the reference pattern and the to-be-inspected pattern. When the relations $a_1=a_2$, $b_1=b_2$ and $a_1 \neq b_1$ are satisfied, it is known that a boundary line parallel to the Y-direction is present in a portion where the operator is placed. The irregularity of pattern corresponding to two or more pixels as shown in part (a) of FIG. 8 is judged to be a defect in the following manner. When the above operator is used on both the to-be-inspected pattern indicated by a solid line in part (a) of FIG. 8 and the reference pattern indicated by a broken line, boundary lines parallel to the Y-direction are detected only in the to-be-inspected pattern. Thus, a pattern portion including the above boundary lines is judged to be a defect. Although only the operator for detecting a boundary line parallel to the Y-direction is shown in part (a) of FIG. 8, an operator for detecting a boundary line parallel to the X-direction is indispensable, and can be formed by revolving the operator shown in part (a) of FIG. 8 through an angle of 90°.

However, an isolated defect shown in part (b) of FIG. 8 and corresponding to one pixel cannot be detected by the above operators. Accordingly, an operator shown in part (b) of FIG. 8 for detecting a fine isolated pattern is indispensable. When this operator is placed on a portion of a pattern and the relation $a_1=a_2=a_3=b_1=b_2=b_3$ and one of the relations $a_1 \neq c_1$, $a_1 \neq c_2$ and $a_1 \neq c_3$ are satisfied, it is known that a fine pattern is present in the portion. When this operator is used on both the to-be-inspected pattern indicated by a solid line in part (b) of FIG. 8 and the reference pattern indicated by a broken line, the fine pattern is detected only in the to-be-inspected pattern, and thus is judged to be a defect. However, in a case where a defect having a length of several pixels along a boundary line and a width of one pixel is present in the vicinity of the boundary line as shown in part (c) of FIG. 8, owing to the alignment error of a to-be-inspected pattern and a reference pattern, a boundary line parallel to the X-direction may be extracted from both of these patterns at substantially the same position by the operator for detecting a boundary line parallel to the X-direction, and thus the defect cannot be detected. Accordingly, an operator shown in part (c) of FIG. 8 is indispensable, and can be formed by revolving the operator shown in part (b) of FIG. 8 through an angle of 90°. Further, in a case where the irregularity of a two-dimensional pattern is present at a corner portion thereof as shown in part (d) of FIG. 8, owing to the alignment error of a to-be-inspected pattern and a reference pattern, one boundary line of the irregularity (namely, defect) parallel to the Y-direction and the boundary line of the reference pattern parallel to the Y-direction may be extracted at substantially the same position, and thus the above defect cannot be detected. Accordingly, an operator shown in part (d) of FIG. 8 is indispensable. When this operator is placed on a portion of a pattern, and a relation $a_1=a_2=a_3=a_4=a_5=a_6=a_7$, a relation $b_1=b_2=b_3=b_4$ and a relation $a_1 \neq b_1$ are all satisfied, it is known that a corner of the pattern is present at the portion. When the operator is used on both the to-be-inspected pattern indicated by a solid line in part (d) of FIG. 8 and the reference pattern indicated by a broken line, the corner is present only in the reference pattern, and thus a defect at the corner portion of the to-be-inspected pattern can be detected. Four kinds of corners can be present in a pattern, and hence four operators are required to detect these corners. As mentioned above, according to the conventional feature comparing method, eight kinds of operators (namely, two kinds of operators for extracting boundary lines, two kinds of operators for extracting fine patterns, and four kinds of operators for extracting corners) are indispensable. Further, eight logic circuits corresponding to eight kinds of operators are provided for each of a to-be-inspected pattern and a reference pattern, and thus sixteen logic circuits are required to detect the above-mentioned defects. Although patterns having only boundary lines parallel to the X- and Y-directions are shown in FIG. 8, a pattern having a more complicated shape is often formed. In order to inspect such a pattern, it is necessary to enlarge the scale of the inspection apparatus.

SUMMARY OF THE INVENTION

It is an object of the present invention to provide a pattern inspection method which can surely detect a defect in a complicated pattern without increasing false information and without enlarging the scale of a pattern inspection apparatus.

In order to attain the above object, according to the present invention, there is provided a pattern inspection method in which a local pattern is cut out of a binary pattern to be inspected, an don't care area is set in the vicinity of the boundary line of the to-be-inspected local pattern, and the to-be-inspected local pattern excepting the don't care area is compared with a corresponding local reference pattern excepting the don't care area, to eliminate false information due to a quantization error, and to detect a defect in the to-be-inspected local pattern without enlarging the scale of a pattern inspection apparatus even when the to-be-inspected local pattern is complicated. Also, a circuit configuration for realizing the above pattern inspection method is herein disclosed, to provide high-speed, highly-reliable defect detection technology.

DESCRIPTION OF THE PREFERRED EMBODIMENTS

An embodiment of a pattern inspection method according to the present invention will be explained below, by reference to FIGS. 1 through 6.

Figure 1:
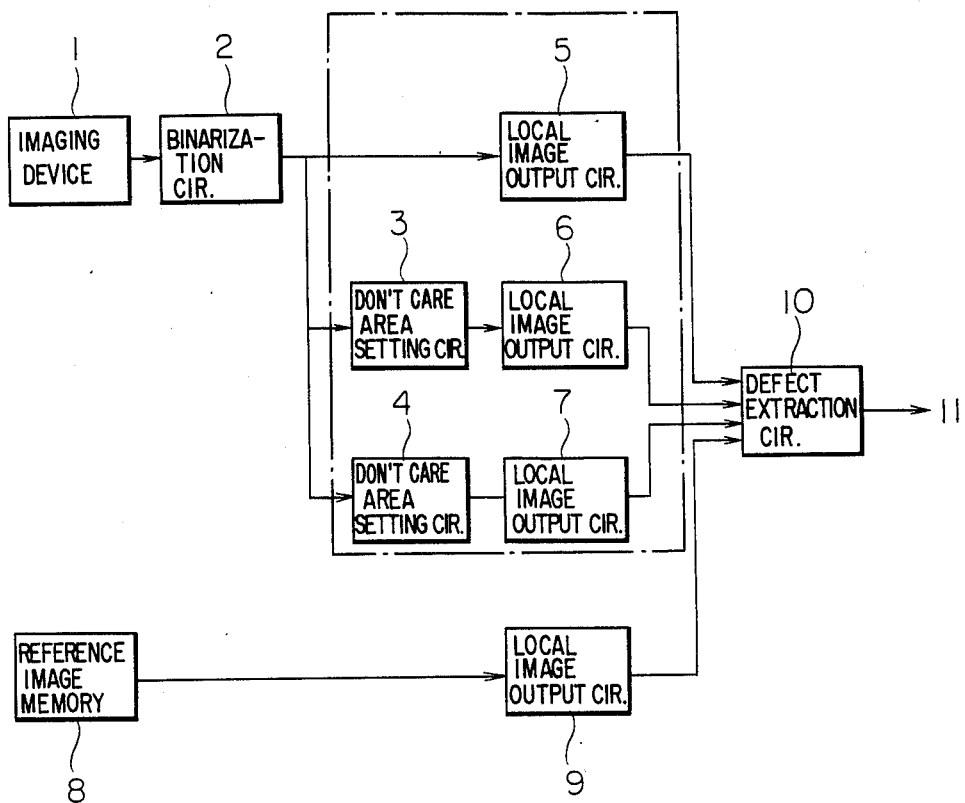
FIG. 1 is a block diagram showing the whole construction of an apparatus for carrying out a pattern inspection method according to the present invention.

FIG. 1 shows an apparatus for carrying out the present embodiment. Referring to FIG. 1, an image signal from a detector (that is, imaging device) 1 is converted by a binarization circuit 2 into a binary signal, which is applied, as a to-be-inspected image, to a local image output circuit 5 and don't care area setting circuits 3 and 4 each for setting an don't care area on the inside or outside of the boundary line of the to-be-inspected image and for extracting the don't care area. The output signals of the don't care area setting circuits 3 and 4 are applied, as don't care area images, to local image output circuits 6 and 7, respectively. While, a reference image signal which is stored in a reference image memory 8 in the form of a binary signal, is applied, as a reference image, to a local image output circuit 9. The reference image memory 8 delivers the reference image signal corresponding to the to-be-inspected image, in synchronism with the scanning operation of the detector 1. A defect is detected by a defect extraction circuit 10 on the basis of the outputs of the local image output circuits 5, 6, 7 and 9, and is delivered as a defect signal 11.

Figure 2:
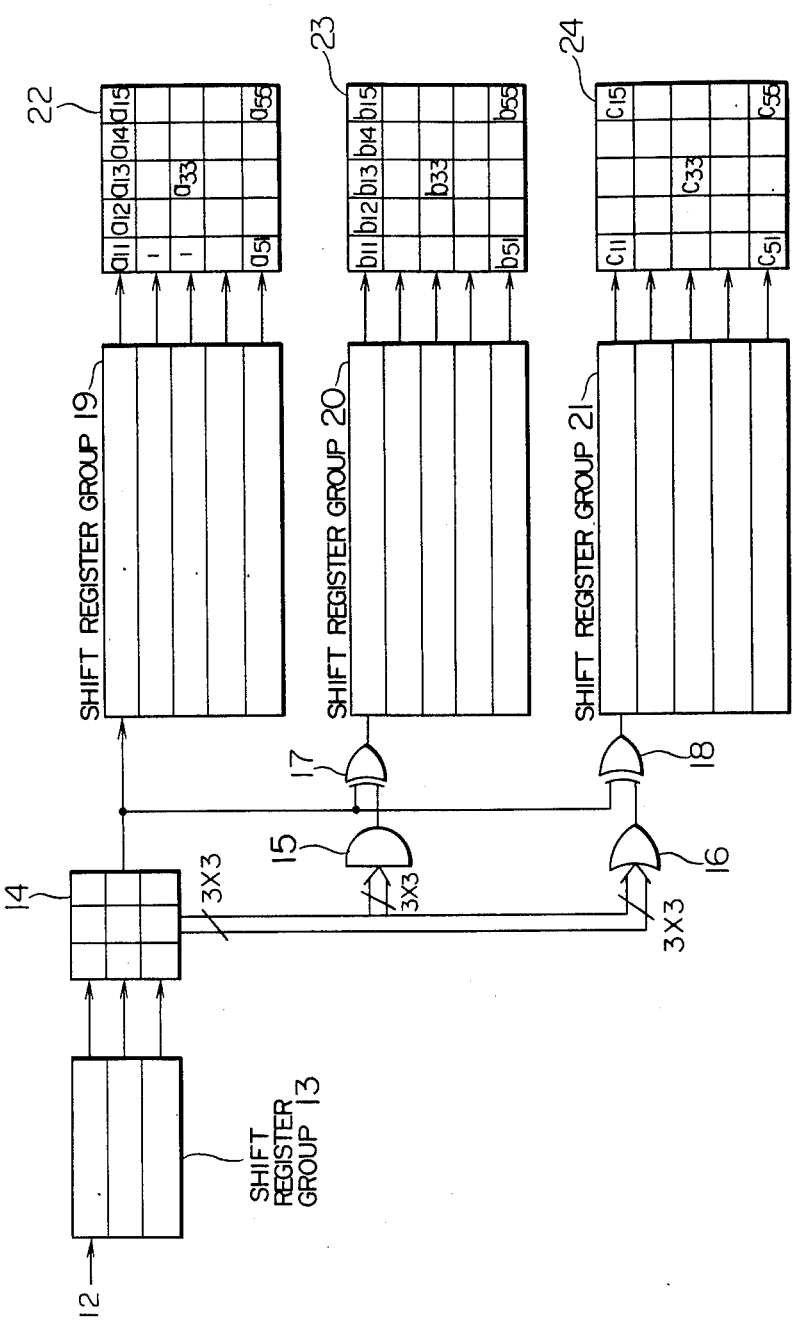
FIG. 2 is a block diagram showing a circuit part which corresponds to the don't care area setting circuits 3 and 4 and the local image output circuits 5, 6 and 7 of FIG. 1, and is used for cutting out a local image and two local don't care area image from an image to be inspected.

FIG. 2 shows the circuit configuration of a circuit part including the don't care area setting circuits 3 and 4 and the local image output circuits 5 to 7. In this circuit configuration, three memories 22 to 24 each including 5×5 pixels are used for enlarging, contracting and judging a boundary portion of the to-be-inspected image, thereby extracting three kinds of boundary portions.

Referring to FIG. 2, an output signal 12 from the binarization circuit 2 of FIG. 1 is applied to a local memory 14 which includes 3×3 bits and is formed of a serial-in parallel-out shift register, through a shift register group 13 which is made up of three shift registers each corresponding to one scanning line on a pattern to be inspected. The 3×3 outputs of the local memory 14 are applied to an AND circuit 15 and an OR circuit 16. A boundary portion which is obtained when an original boundary portion is contracted by an amount corresponding to one pixel, is outputted from the AND circuit 15, and a boundary portion which is obtained when the original boundary portion is enlarged by an amount corresponding to one pixel, is delivered from the OR circuit 16. The output from the center pixel of the local memory 14 and the output of the AND circuit 15 are applied to an EXCLUSIVE-OR circuit 17, and thus an don't care area signal taking a level "1" in an area which has a width of one pixel along an original boundary line on the inside thereof, is delivered from the EXCLU- SIVE-OR circuit 17. Further, the output from the center pixel of the local memory 14 and the output of the OR circuit 16 are applied to another EXCLUSIVE-OR circuit 18, and thus an don't care area signal which takes the level "1" in an area which has a width of one pixel along the original boundary line on the outside thereof, is delivered from the EXCLUSIVE-OR circuit 18.

Figure 3:
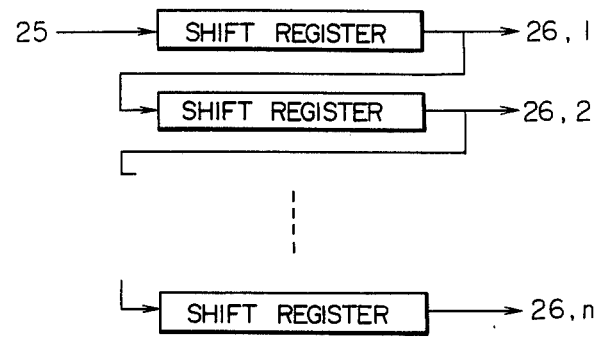
FIG. 3 is a block diagram showing the construction of each of shift register groups used in the apparatus of FIG. 1.

Next, explanation will be made of a circuit part for cutting out a local image having 5×5 pixels from the to-be-inspected image, an inside don't care area image and an outside don't care area image. The output from the center pixel of the local memory 14, the output of the EXCLUSIVE-OR circuit 17 and the output of the EXCLUSIVE-OR circuit 18 are applied to the local memories 22, 23 and 24 through shift register groups 19, 20 and 21, respectively. Each of the local memories 22 to 24 is formed of a serial-in parallel-out shift register and includes 5×5 pixels. Each of the shift register groups 19 to 21 is made up of five shift registers each corresponding to one scanning line on the to-be-inspected pattern. Thus, local images each including 5×5 pixels and cut out from the to-be-inspected image are successively applied to the local memory 22, local images each including 5×5 pixels and cut out from the inside don't care area image are successively applied to the local memory 23, and local images each including 5×5 pixels and cut out from the outside don't care area image are successively applied to the local memory 24. FIG. 3 shows the construction of an example of shift register groups used in the apparatus of FIG. 1. Referring to FIG. 3, n shift registers are connected in series, and individual shift registers deliver outputs 26.1, 26.2, ... and 26.n. Incidentally, as shown in FIG. 3, an input signal 25 is applied to the first shift register.

Figure 4:
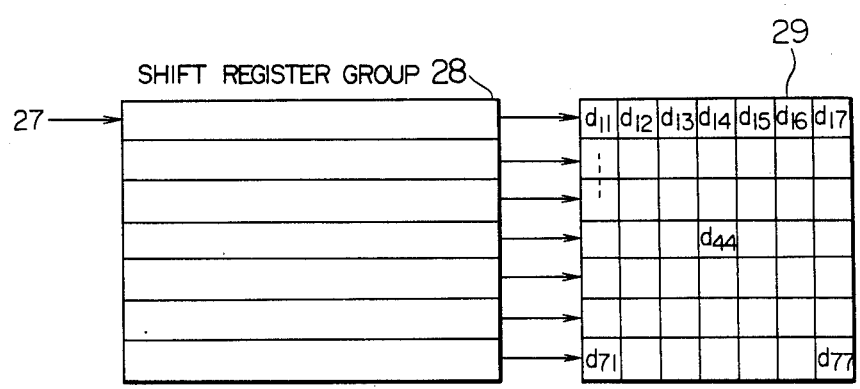
FIG. 4 is a block diagram showing a circuit part for cutting out a local image from the image of a designed pattern (namely, a reference pattern).

FIG. 4 shows a circuit part for cutting out a local image from the image of the designed pattern (namely, reference pattern). In general, the alignment error of the to-be-inspected pattern and the reference pattern is unavoidable. Accordingly, when a local image is cut out from the image of the reference pattern (namely, the reference image) to obtain a local reference image corresponding to the local image on the local memory 22, it is necessary to make the local image which is cut out from the reference image, larger than the local image on the local memory 22 by an amount corresponding to the alignment error, so that a portion of the local image cut out from the reference image corresponds to the local image on the local memory 22. FIG. 4 shows a case where the alignment error in each of X- and Y-directions is ±one pixel at most.

A local image on each of the local memories 22 to 24 includes 5×5 pixels. In a case where the above local image can shift from the corresponding local reference image by ±one pixel in each of the X- and Y-directions, a local reference image including 7×7 pixels has to be cut out from the reference image, as shown in FIG. 4. Referring to FIG. 4, a reference image signal 27 is applied to a local memory 29 including 7×7 pixels through a shift register group 28 which is made up of seven shift registers each corresponding to one scanning line on the to-be-inspected pattern. Further, the reference image signal 27 is read out from the reference image memory 8 of FIG. 1 in synchronism with the scanning operation of the detector 1 so that, when the to-be-inspected pattern is accurately located in relation to the reference pattern (that is, the alignment error is zero), the center pixel $d_{44}$ of the local memory 29 and the center pixel $a_{33}$ of the local memory 22 indicate corresponding portions of the to-be-inspected and reference patterns.

Figure 5:
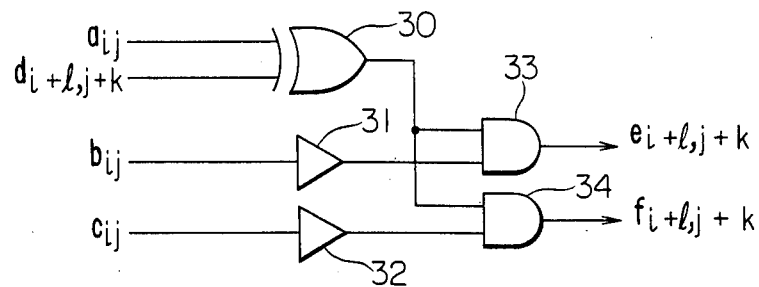
FIG. 5 is a circuit diagram showing the circuit configuration of the defect extraction circuit 10 of FIG. 1.
Figure 5:
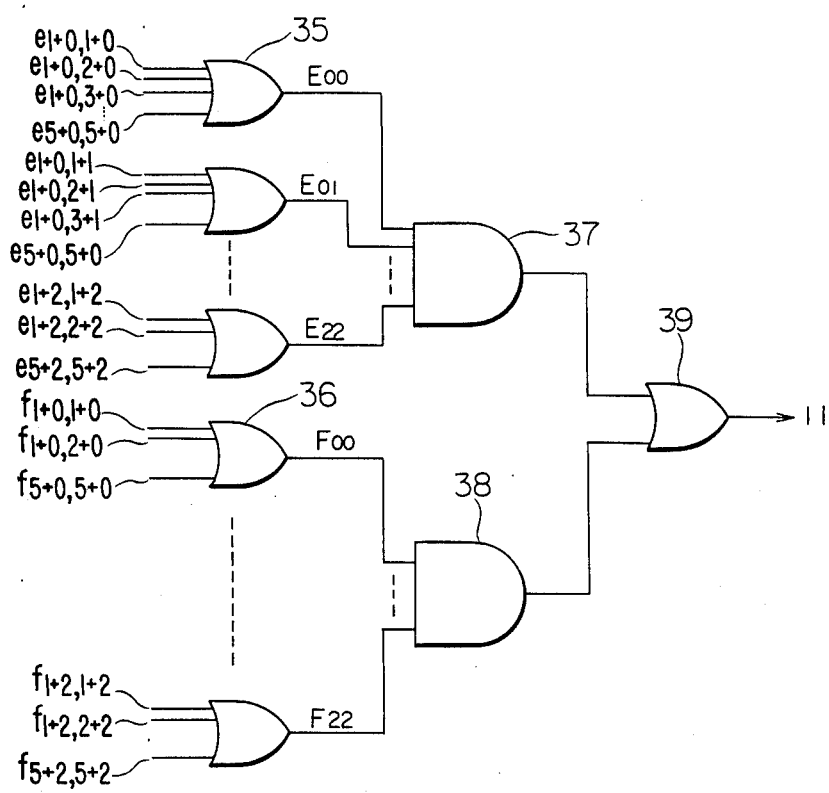

FIG. 5 shows the detailed circuit configuration of the defect extraction circuit 10 for judging a defect by the local images on the local memories 22, 23, 24 and 29. In FIG. 5, symbols $a_{ij}$, $b_{ij}$ and $c_{ij}$ (where i=1, 2, 3, 4 and 5, j=1, 2, 3, 4 and 5) designate the output of each pixel of the local memory 22, the output of each pixel of the local memory 23 and the output of each pixel of the local memory 24, respectively, and $d_{i+l, j+k}$ (where i=1, 2, 3, 4 and 5, j=1, 2, 3, 4 and 5, l=0, 1 and 2, k=0, 1 and 2) the output of each pixel of the local memory 29. Values of l equal to 0, 1 and 2 are added to each of values of i equal to 1, 2, 3, 4 and 5, and values of k equal to 0, 1 and 2 are added to each of values of j equal to 1, 2, 3, 4 and 5. The output $a_{ij}$ and the output $d_{i+l,j+k}$ are applied to an EXCLUSIVE-OR circuit 30. Such logical processing means that the local image obtained on the local memory 22 is moved on the local image obtained on the local memory 29, and an EXCLUSIVE-OR operation is performed for a pair of pixels at the same position, to deliver the result of the EXCLUSIVE-OR operation for each pixel pair, from the EXCLUSIVE-OR circuit 30. Further, the output of each pixel of the local don't care area image, obtained on the local memory 23 is applied to a NOT circuit 31, the output of which is applied to an AND circuit 33 together with the output of the EXCLUSIVE-OR circuit 30. Similarly, the output of each pixel of the local don't care area image obtained on the local memory 24 is applied to a NOT circuit 32, the output of which is applied to an AND circuit 34 together with the output of the EXCLUSIVE-OR circuit 30. Thus, a signal indicating whether or not the local image on the local memory 22 agrees with a local reference image including 5×5 pixels when the don't care area on the local memory 23 is neglected, is delivered from the AND circuit 33. Similarly, a signal indicating whether or not the local image on the local memory 22 agrees with a local reference image including 5×5 pixels when the don't care area on the local memory 24 is neglected, is delivered from the AND circuit 34. The upper portion of the circuit of FIG. 5, including the EXCLUSIVE-OR circuit 30, AND circuits 33 and 34, and NOT circuits 31 and 32 comprises 225 circuit elements in this example, since suffixes i, j take values from 1 to 5 and the suffices l and k take values from 0 to 2, and so 5×5×3×3=225. The output of the AND circuit 33 corresponding to each value of l and k is applied to a corresponding one of OR circuits 35, and the output of the AND circuit 34 corresponding to each value of l and k is applied to a corresponding one of OR circuit 36. That is, 5×5 outputs from 5×5 pixels of a local image given by the output of the AND circuit 33 or 34 are applied to one of the OR gates 35 or 36. The outputs of the OR circuits 35 are applied to an AND circuit 37, and the outputs of the OR circuits 36 are applied to an AND circuit 38. The outputs of the AND circuits 37 and 38 are applied to an OR circuit 39, to deliver a defect signal 11 from the OR circuit 39. According to such a circuit configuration, the output $E_{lk}$ of one of the OR circuits 35 indicates whether or not the local to-be-inspected image on the local memory 22 agrees with a corresponding local reference image including 5×5 pixels in a case where the to-be-inspected pattern deviates from the reference pattern in the X-direction by (l−1) pixels and in the Y-direction by (k−1) pixels, if the inside don't care area on the local memory 23 is removed from these local images. Further, the output $F_{lk}$ of one of the OR circuit 36 indicates whether or not the local to-be-inspected image on the local memory 22 agrees with a corresponding local reference image including 5×5 pixels in the above case, if the outside don't care area on the local memory 24 is removed from these local images. When at least one of the outputs $E_{lk}$ (where l=0, 1 and 2, k=0, 1 and 2) indicates agreement, the output of the AND circuit 37 takes a level "0". When all the outputs $E_{lk}$ indicate disagreement, the output of the AND circuit 37 takes a level "1". When at least one of the outputs $F_{lk}$ indicates agreement, the output of the AND circuit 38 takes a level "0". When all the outputs $F_{lk}$ indicate the disagreement, the output of the AND circuit 38 takes a level "1". When both of the outputs of the AND circuits 37 and 38 indicate agreement, the output of the OR circuit 39 takes a level "0" to show the absence of a defect. When at least one of the outputs of the AND circuits 37 and 38 indicates disagreement, the output of the OR circuit 39 takes a level "1" to show the presence of a defect.

Figure 6:
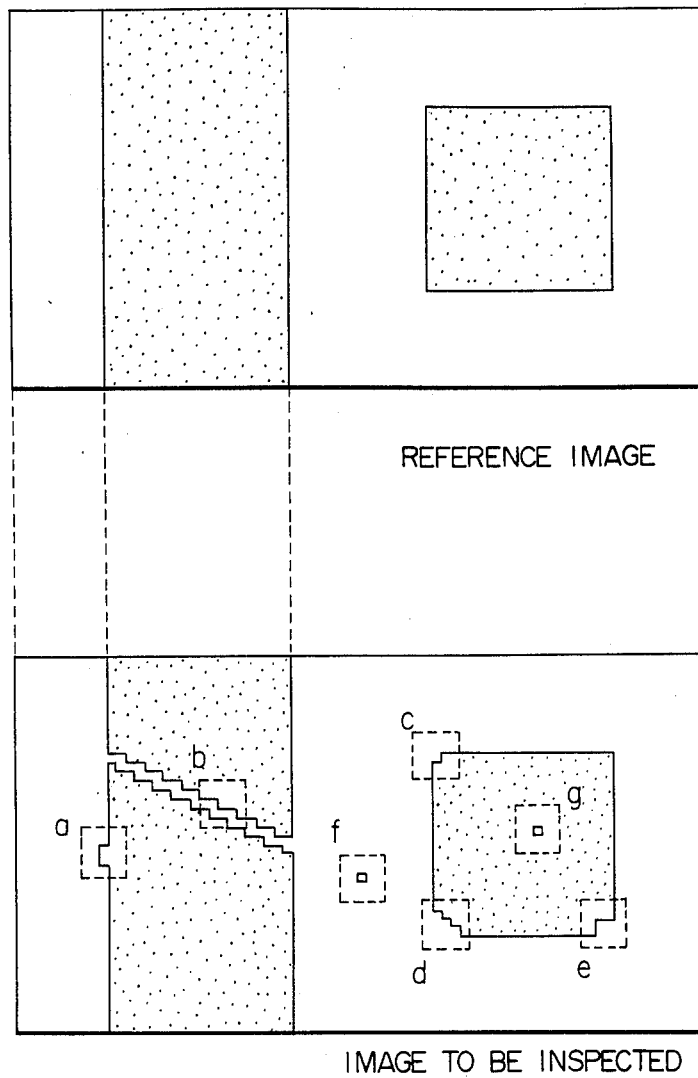
FIG. 6 is a schematic diagram showing a reference image and a corresponding to-be-inspected image having various defects.
Figure 7A:
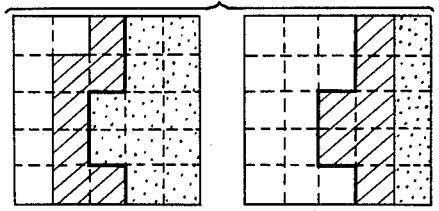
FIGS. 7(a), 7(b), 7(c), 7(d), 7(e), 7(f) and 7(g) are schematic diagrams showing don't care areas which are set on the outside and inside of the boundary line of each of the defects shown in FIG. 6 to cause the apparatus of FIG. 1 to perfrm a predetermined operation independently of the kind of each defect.
Figure 7E:
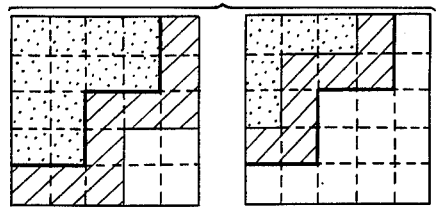
Figure 7B:
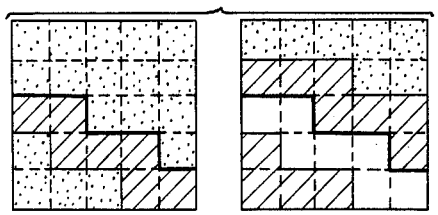
Figure 7F:
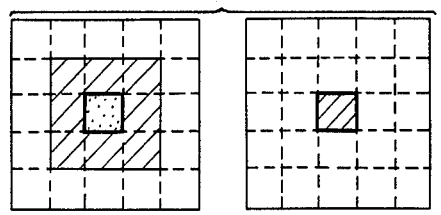
Figure 7C:
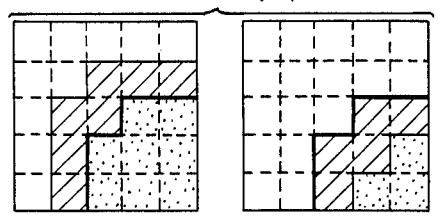
Figure 7G:
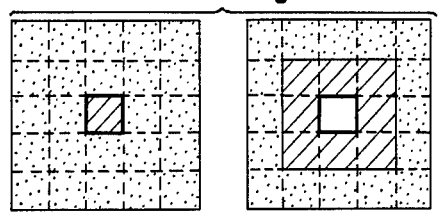
Figure 7D:
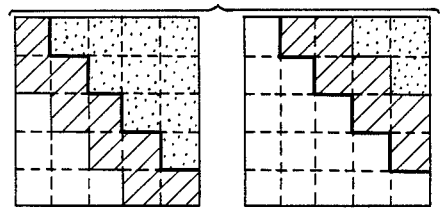
Figure 8:
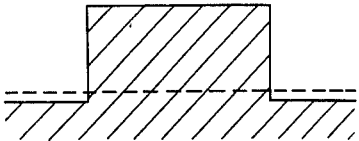
FIG. 8 is a schematic diagram for explaining that in order to detect various kinds of defects by a conventional feature extraction method, it is necessary to prepare extraction operators corresponding to the defects.
Figure 8:
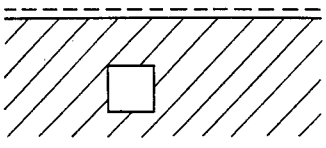
Figure 8:
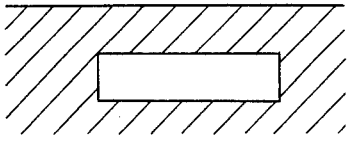
Figure 8:
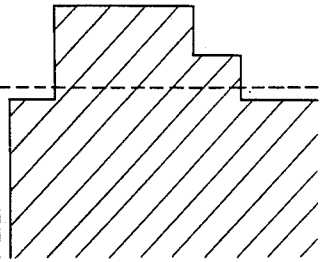

Now, let us consider a case where the present invention is applied to a to-be-inspected image and a reference image which are shown in FIG. 6. In FIG. 6, reference characters a to g designate local areas of the to-be-inspected image. FIG. 7 shows how each of the local areas a to g is expressed on the local memories 23 and 24. According to the present invention, irregularities in the local areas b, d, e, f and g are extracted as defects, but irregularities in the local areas a and c are not considered to be defects since these irregularities can be regarded as quantization errors.

As can been seen from the above explanation, according to the present invention, even when a pattern to be inspected is complicated, defects in the pattern can be detected without modifying the structure of an inspection apparatus and a defect extracting method.

In the above explanation, a designed pattern has been used as the reference pattern. However, the present invention is also applicable to a case where the image of a body having the same shape as the to-be-inspected pattern is formed by an imaging device and the image thus obtained is used as the reference image.

Further, it is not always necessry to the present invention that an image signal indicating a reference pattern and an image signal indicating a pattern to be inspected are simultaneously formed by imaging devices and converted into binary image signals, and local images are simultaneously taken out of these image signals to be compared with each other, but the present invention is applicable to, for example, a case where an image signal indicating one of a plurality of patterns having the same shape is previously stored in a memory, and the image signal read out from the memory is compared with each of the image signals indicating the remaining patterns.

We claim:
1. A pattern inspection apparatus comprising:
an image device for detecting a to-be-inspected pattern;
conversion means for converting an image signal from said image device to a binary pixel signal;
first cut-out means including a first shift register group for cutting out said binary pixel signal and for storing the cut-out signal into first memory means having n×n memory elements;
first don't care area forming means for taking a logical product of pixels two-dimensionally stored in said first memory means of said first cut-out means and for taking an exclusive logical addition between a result of said logical product and a center pixel in said first memory means to form a don't care area covering a scope of quantization error on one side of an edge of said to-be-inspected pattern;
second don't care area forming means for taking a logical addition of pixels two-dimensionally stored in said first memory means in said first cut-out means and for taking an exclusive logical addition between a result of said logical addition and the center pixel in said first memory means to form another don't care area covering the scope of the quantization error on another side of the edge of said to-be-inspected pattern;
second cut-out means including a second shift register group for cutting out output signals from the center of said first memory means and for storing the cut-out signals into a second memory means having m×m memory elements arranged in i columns and k rows;
third cut-out means including a third shift register group for cutting out output signals from said one don't care area forming means and for storing the cut-out signals as don't care signals into third memory means having m×m memory elements arranged in i columns and j rows;
fourth cut-out means including a fourth shift register group for cutting out output signals from said another don't care area forming means and for storing the cut-out signals as don't care signals into fourth memory means having elements in i columns and j rows;
reference pattern means for generating binary pixel signals of a reference pattern;
fifth cut-out means including a fifth shift register group for cutting out the binary signals from said reference pattern means and for storing the cut-out signals into fifth memory means having $(m+\alpha) \times (m+\alpha)$ memory elements arranged in i+1 columns and j+k rows in synchronism with operation of said second, third and fourth cut-out means;
means including $m \times m \times \alpha \times \alpha$ first logic circuits, each for detecting a signal representative of disagreement between a respective element $a_{ij}$ in said second memory means and a respective element $d_{i+l,j+k}$ in said fifth memory means to output a first comparison signal $e_{i+l,j+k}$ by blocking disagreement by a respective element of the don't care signal in said third memory means and to output a second comparison signal $f_{i+l,j+k}$ by blocking disagreement by a respective element $c_{ij}$ of the don't care signal in said fourth memory means; and
means including a second logic circuit for taking a logical addition to said first and second comparison signals $e_{i+l,j+k}$ and $f_{i+l,j+k}$ from said first logic circuits when the values l and k are shifted from 0 to $\alpha$, respectively to output first and second simulation defect signals $E_{l,k}$ and $F_{l,k}$ when said logical addition detects disagreement at any one of values of i of 1 to m and j of 1 to m and then output read defect signal when the simulation defect signals are detected about all the results of said logical addition over l of 0 to $\alpha$ and k of 0 to $\alpha$ at least one of the results $E_{l,k}$ and $F_{l,k}$ of said logical addition.

2. A pattern inspection apparatus according to claim 1, wherein each first logic circuit includes an EXCLUSIVE OR circuit having a first input connected to receive an element $a_{ij}$ from said second memory means and a second input connected to receive an element $d_{i+l, j+k}$ from said fifth memory means, a first AND gate having one input connected to receive the output of said EXCLUSIVE OR circuit, another input connected to receive an element $b_{ij}$ from said third memory means and an output providing said first comparison signal.

3. A pattern inspection apparatus according to claim 2, wherein each first logic circuit further includes a second AND gate having one input connected to receive the output of said EXCLUSIVE OR circuit, another input connected to receive an element $c_{ij}$ from said fourth memory means and an output providing said second comparison signal.

* * * * *